(12) United States Patent
Brown

(10) Patent No.: US 11,191,664 B2
(45) Date of Patent: Dec. 7, 2021

(54) MANDIBULAR ADVANCEMENT DEVICE

(71) Applicant: Brown Innovation, LLC, Lake Quivira, KS (US)

(72) Inventor: Thomas W. Brown, Lake Quivira, KS (US)

(73) Assignee: Brown Innovation, LLC, Lake Quivira, KS (US)

( * ) Notice: Subject to any disclaimer, the term of this patent is extended or adjusted under 35 U.S.C. 154(b) by 180 days.

(21) Appl. No.: 16/705,723

(22) Filed: Dec. 6, 2019

(65) Prior Publication Data
US 2021/0169679 A1 Jun. 10, 2021

(51) Int. Cl.
*A61F 5/56* (2006.01)
*A61F 5/58* (2006.01)

(52) U.S. Cl.
CPC ............... *A61F 5/566* (2013.01); *A61F 5/56* (2013.01); *A61F 5/58* (2013.01); *A61F 2005/563* (2013.01)

(58) Field of Classification Search
CPC .... A61F 5/56; A61F 5/566; A61F 5/58; A61F 5/05891; A61F 2005/563; A63B 71/085; A61C 7/08; A61C 7/36; A61C 7/12; A61C 7/10; A61B 5/08; A61B 5/4818; A61B 5/0488; A61M 16/0488; A61M 16/049; A61M 16/0493; Y10S 602/902

USPC ................... 128/846, 848, 859, 861, 862
See application file for complete search history.

(56) References Cited

U.S. PATENT DOCUMENTS

| | | | |
|---|---|---|---|
| 10,342,694 B1 * | 7/2019 | Mowell | A61F 5/566 |
| 2010/0206314 A1 * | 8/2010 | Brown | A61F 5/566 128/861 |
| 2018/0360646 A1 * | 12/2018 | Bedford | A61F 5/566 |
| 2020/0222227 A1 * | 7/2020 | Shim | A61F 5/566 |

FOREIGN PATENT DOCUMENTS

CA 3007171 A1 * 12/2018 ............. A61F 5/566

* cited by examiner

*Primary Examiner* — Alireza Nia
*Assistant Examiner* — Daniel A Miller
(74) *Attorney, Agent, or Firm* — Hovey Williams LLP

(57) ABSTRACT

A customizable mandibular advancement device for use in treating snoring and obstructive sleep apnea is provided. The device comprises upper and lower trays adapted to be fitted to a person's maxillary and mandibular arches. The upper tray comprises a stop member, which when engaged with a fin located on the lower tray, inhibits the posterior movement of the user's mandible thereby maintaining the mandible in an advanced position. Both the upper and lower trays comprise a core that is overmolded by a thermoplastic material that has a much lower softening temperature than the core.

16 Claims, 13 Drawing Sheets

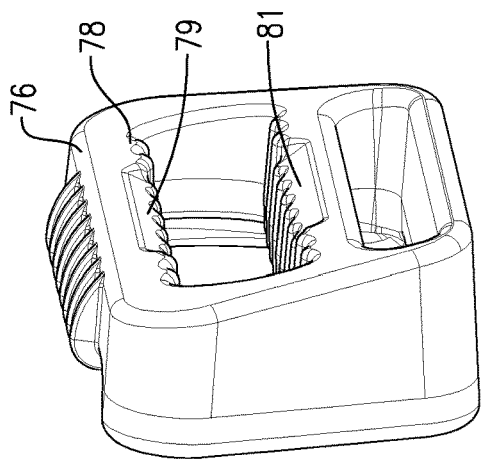
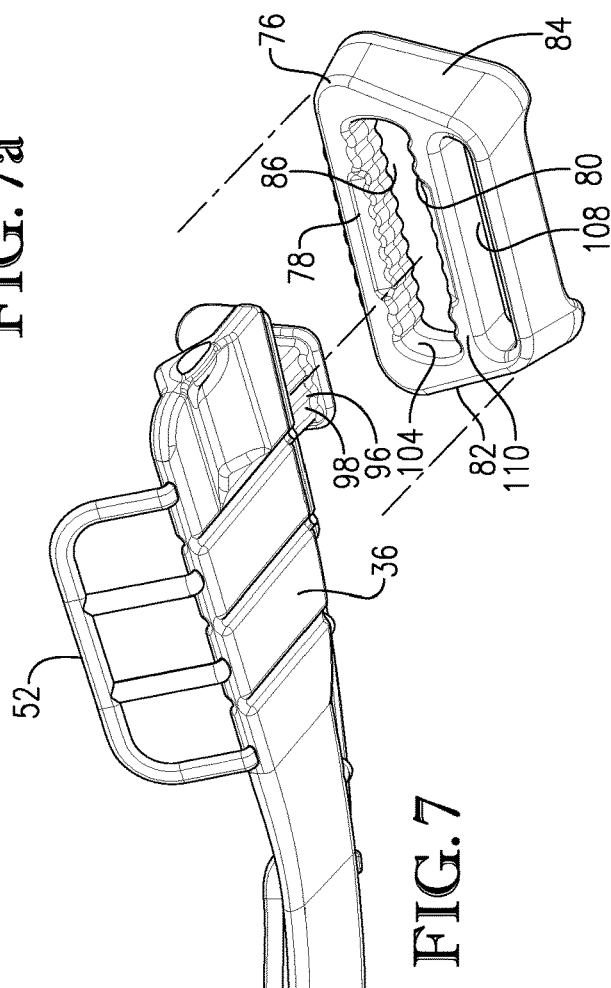
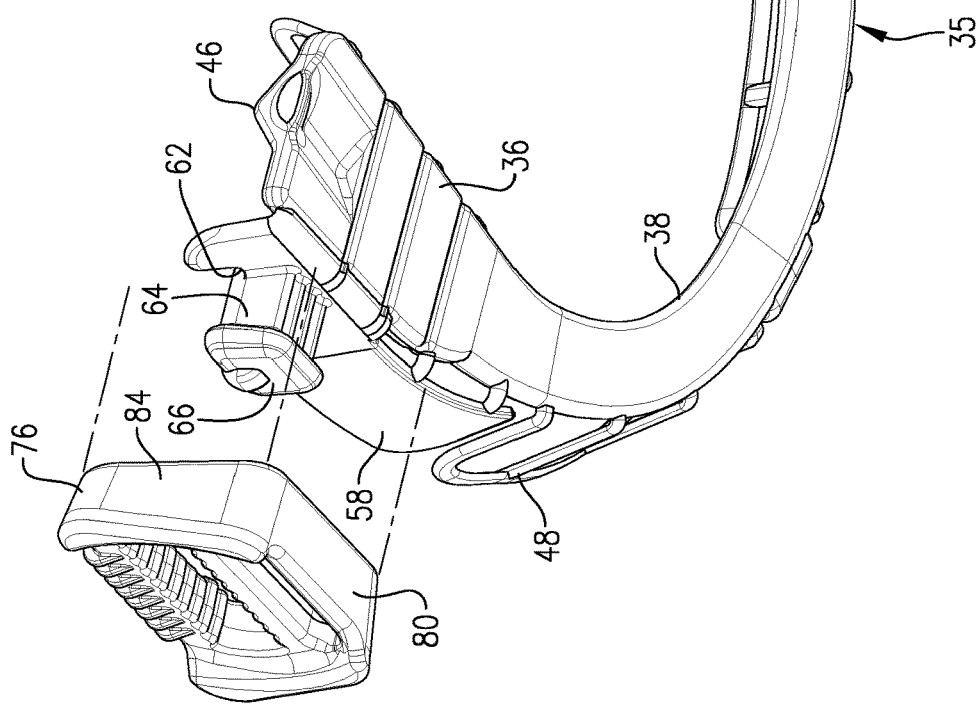

MANDIBULAR ADVANCEMENT DEVICE

BACKGROUND OF THE INVENTION

Field of the Invention

The present invention is generally directed toward a customizable mandibular advancement device for use in treating snoring and obstructive sleep apnea. The device comprises an upper tray adapted to be fitted to a person's maxillary teeth, and a lower tray adapted to be fitted to a person's mandibular teeth. Each tray comprises a core that is overmolded by a thermoplastic material that has a much lower softening temperature than the core.

Description of the Prior Art

Obstructive sleep apnea occurs when the muscles in the back of a person's throat relax thereby weaking support for the soft palate, uvula, tonsils and tongue. As the muscles that support these structures relax, the person's airway narrows, leading to impaired breathing, and oftentimes, excessively loud snoring. Obstructive sleep apena can have a number of unpleasant, and even dangerous, health consequences.

In some cases, obstructive sleep apnea can be treated with a dental appliance that is designed to maintain the user's mandible in a neutral or advanced position so that when the user's throat muscles relax the mandible does not shift rearwardly and further constrict the user's airway. Often, these dental appliances are made by lab after a dentist has taken impressions of the patient's teeth. Notwithstanding the fact that large segments of the public have difficulty in accessing dental care (there are approximately 150,000 dentists in the U.S. serving 350 million people), these professionally made appliances are expensive and unaffordable to many consumers. In addition, these professionally made appliances are often formed from a thick and rigid plastic material that is thick and creates significant separation between the user's maxillary and mandibular arches. Thus, these appliances can result in the inability to fully close one's lips during sleep leading to dry mouth, chapped lips, or other annoyances. Also, the bulk of these appliances make it difficult to speak or drink while being worn.

Other types of mandibular advancement devices use a Herbst mechanism that is connected to the upper and lower tray structures for maintaining the lower tray in an advanced position. However, these devices also are quite bulky and must be inserted into and removed from the user's mouth as a unit rather than as smaller, individual pieces. Again, these devices make it difficult for the wearer to speak and drink while being worn.

Therefore, a need exists for a mandibular advancement device that has a slimmer profile that is more comfortable for the user and can be custom fitted by the end user rather than requiring fitting by a dental professional.

SUMMARY OF THE INVENTION

According to one embodiment of the present invention a mandibular advancement device is provided that comprises an upper tray adapted to be fitted over a user's maxillary arch and a lower tray adapted to be fitted over the user's mandibular arch. The upper tray comprises a pair of adjustable stop members, and the lower tray comprises a pair of fins extending from the lower tray. Each of the fins are configured to engage a respective stop member to inhibit posterior movement of the lower tray when worn by the user. Each of the upper and lower trays comprise a core formed from a first material having a first softening point temperature and an outer layer overmolded onto the core. The outer layer is formed from a second material having a second softening point temperature that is less than the first softening point temperature.

According to another embodiment of the present invention a mandibular advancement device is provided that comprises an upper tray adapted to be fitted over a user's maxillary arch and a lower tray adapted to be fitted over the user's mandibular arch. Each of the upper and lower trays comprise a core formed from a first material having a first softening point temperature and an outer layer overmolded onto the core. The outer layer is formed from a second material having a second softening point temperature that is less than the first softening point temperature. The upper tray comprises a pair of posts extending laterally from respective buccal sidewalls of the upper tray core, and an adjustable stop member attached to each post. The lower tray comprises a pair of fins that extend laterally from the lower tray core. Each of the fins are configured to engage a respective stop member to inhibit posterior movement of the lower tray when worn by the user. Each post further comprises a button disposed at the outboard end thereof that is configured to retain the stop member on the post.

According to yet another embodiment of the present invention a method of treating obstructive sleep apnea is provided. The method comprises fitting a mandibular advancement device, comprising upper and lower trays as described herein, to the maxillary and mandibular arches of a user. The fitting step comprises heating the upper and lower trays to a temperature of about 40° C. to about 80° C. thereby causing the overmolded outer layer of each tray to soften. The softened outer layer of the upper tray is molded to at least some of the user's maxillary teeth, and the softened outer layer of the lower tray is molded to at least some of the user's mandibular teeth. The softened outer layer of the upper and lower trays is permitted to harden within the user's mouth. The pair of adjustable stop members are adjusted to a position that is sufficient to maintain the mandible in an advanced position when the device is being worn by the user.

BRIEF DESCRIPTION OF THE DRAWINGS

FIG. 7 is an exploded view of the upper tray's inner core and adjustment members;

FIG. 7a is a view of the lingual side of the adjustment member;

DETAILED DESCRIPTION OF THE PREFERRED EMBODIMENT

Figure 1:
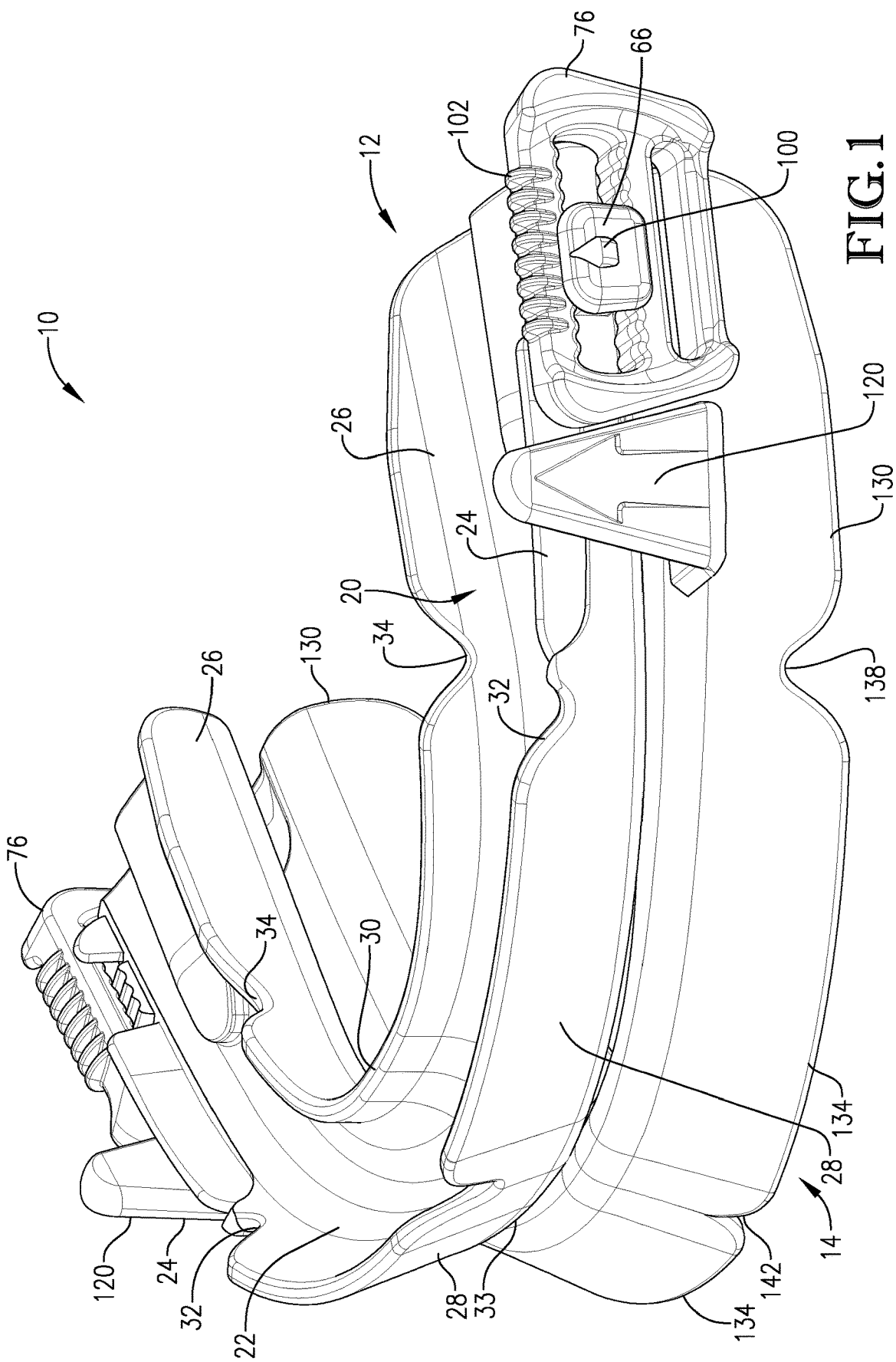
FIG. 1 is a top perspective view of an embodiment of a mandibular advancement device according to the present invention.
Figure 2:
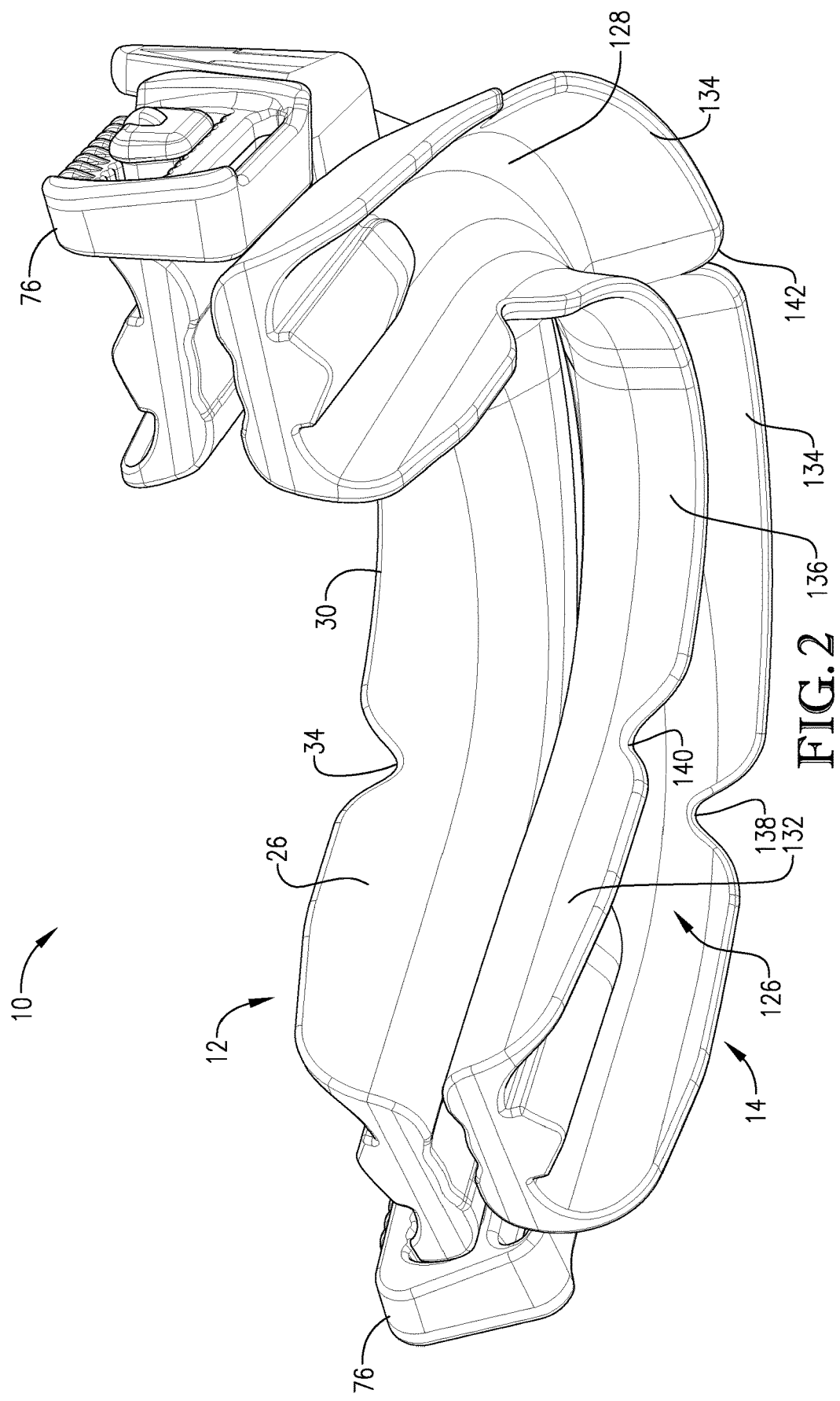
FIG. 2 is a bottom perspective view of the mandibular advancement device of FIG. 1.

FIGS. 1 and 2 depict a mandibular advancement device 10 in accordance with an embodiment of the present invention. Device 10 comprises an upper tray 12 that is adapted to be fitted and worn over a user's maxillary arch and a lower tray 14 that is adapted to be fitted and worn over the user's mandibular arch. The upper tray 12 and lower tray 14 are preferably constructed in accordance with the concepts described in U.S. Patent Application Publication No. 2018/0344508, by the same inventor, and which is incorporated by reference herein in its entirety.

Figure 3:
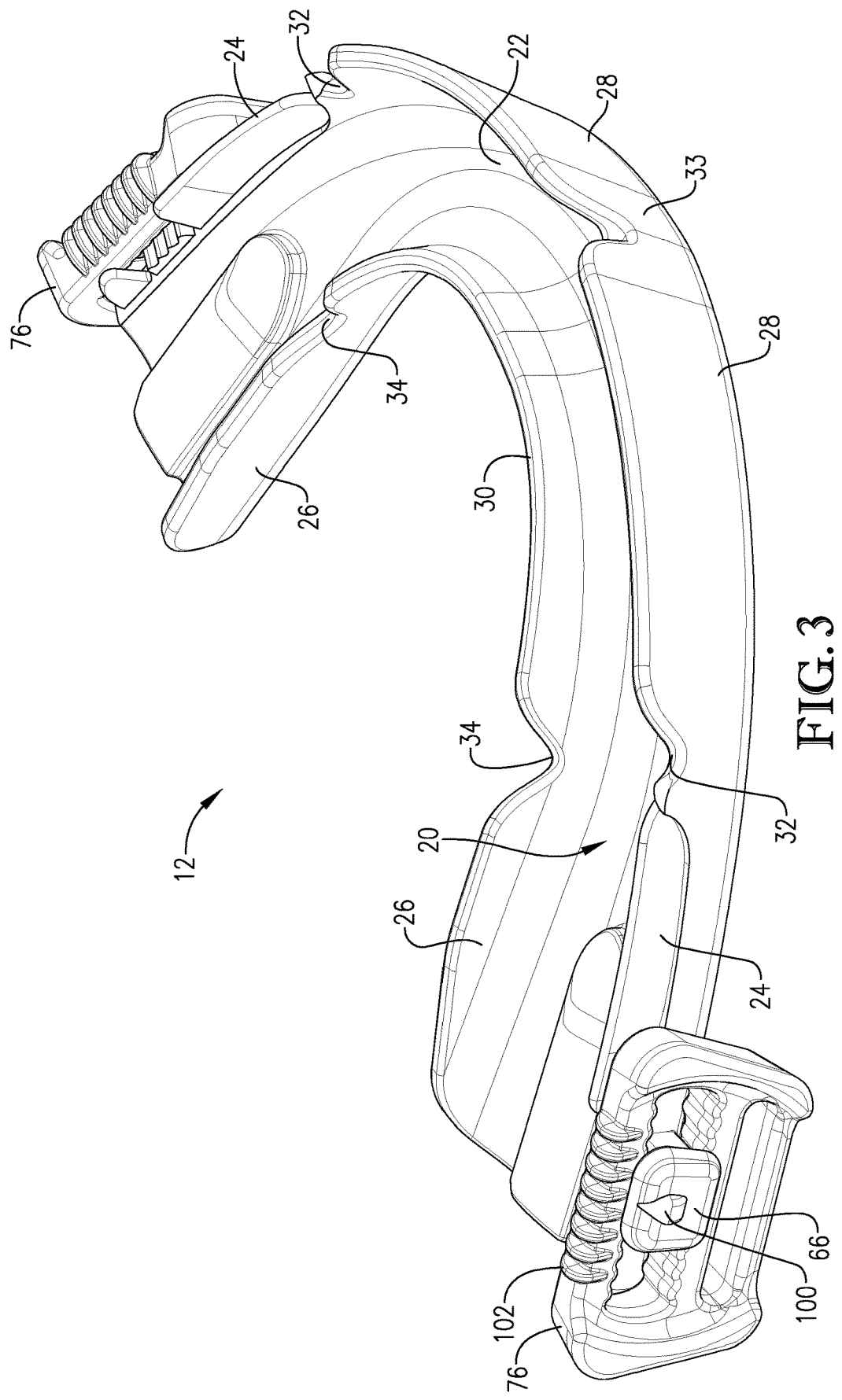
FIG. 3 is a top perspective view of the upper tray of the mandibular advancement device of FIG. 1.
Figure 4:
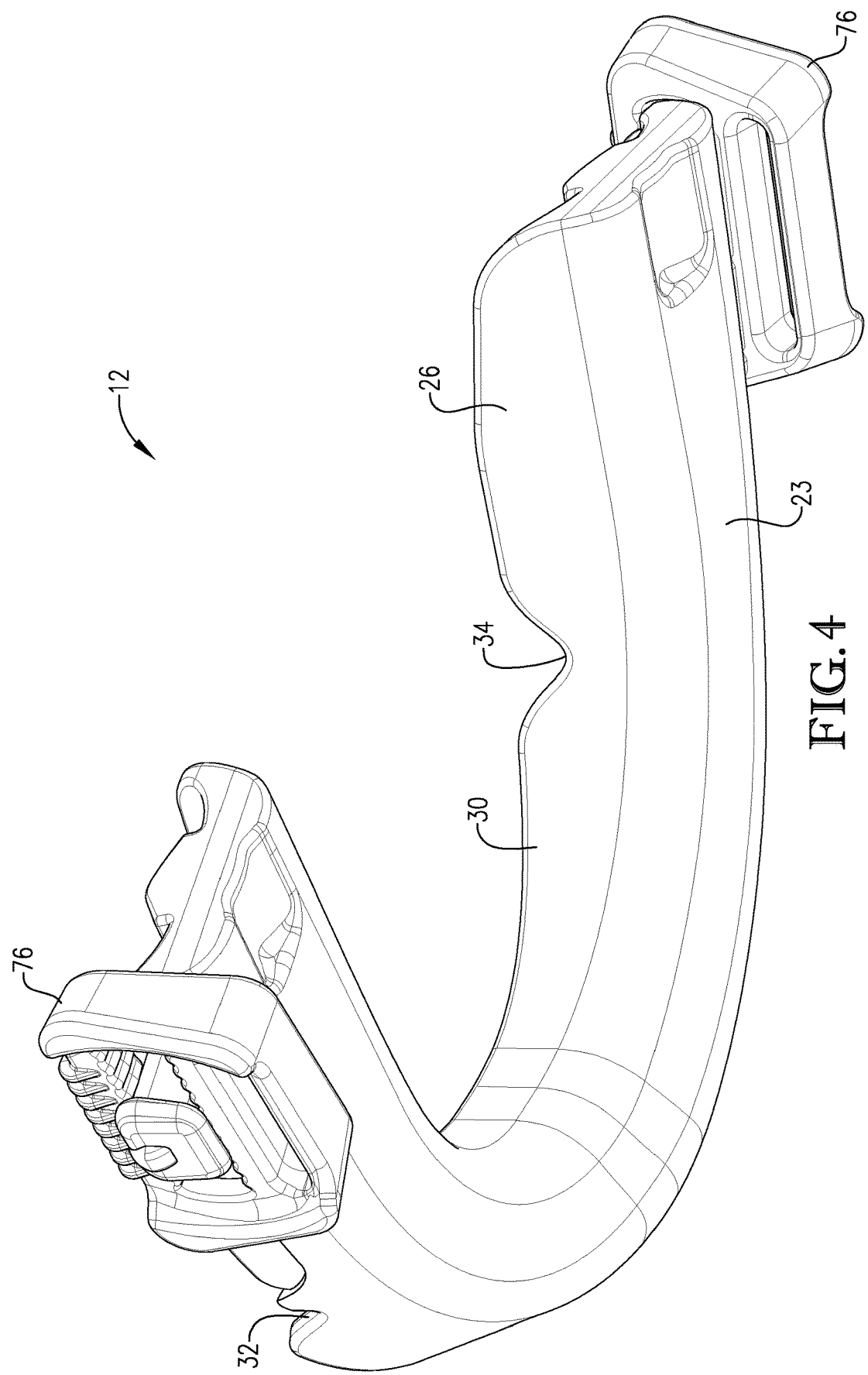
FIG. 4 is a bottom perspective view of the upper tray of the mandibular advancement device of FIG. 1.

Upper tray 12 comprises an inner core 16 (see, FIGS. 5-7) that is overmolded by an outer layer 18. The inner core 16 comprises a first material, preferably a thermoplastic polymeric material that has a first softening point temperature. The outer layer 18 comprises a second material, preferably a thermoplastic polymeric material, that has a second softening point temperature, which is less than the first softening point temperature. The outer layer 18 is configured to define, at least in part a channel 20 that is adapted to receive at least some of the maxillary teeth of a user. As depicted in FIGS. 3-4, the channel 20 comprises a maxillary occlusal surface 22, and preferably buccal sidewalls 24 and lingual sidewalls 26. In certain embodiments, upper tray 12 further comprises a facial sidewall 28 and an anterior palatal sidewall 30. The various sidewalls that assist in defining channel 20 are formable to the contours of the user's maxillary teeth during customization of the upper tray. Thus, tray 12 may further comprise labial recesses 32 in between buccal sidewalls 24 and the facial sidewall 28, and lingual recesses 34 in between lingual sidewalls 26 and anterior palatal sidewall 30. In addition, an anterior recess 33 may be provided between adjacent facial sidewalls 28. Recesses 32, 33, 34 provide space into which the thermoplastic material comprising the various sidewalls may be displaced during custom fitting of tray 12. In addition, recesses 32, 33, 34 provide passageways for drainage of saliva from the channel 20, as necessary.

Figure 5:
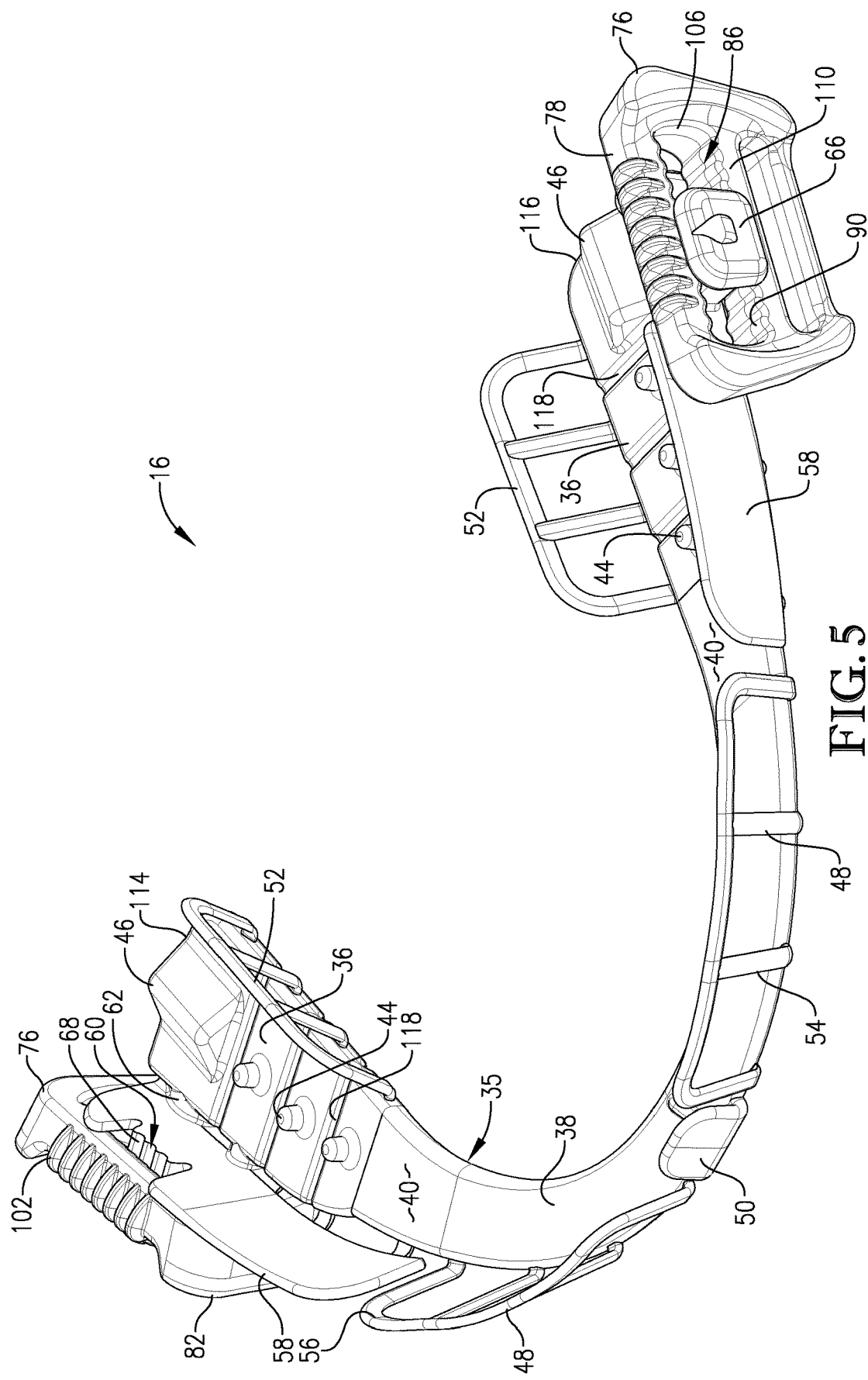
FIG. 5 is a top perspective view of the upper tray's inner core and adjustment members.
Figure 6:
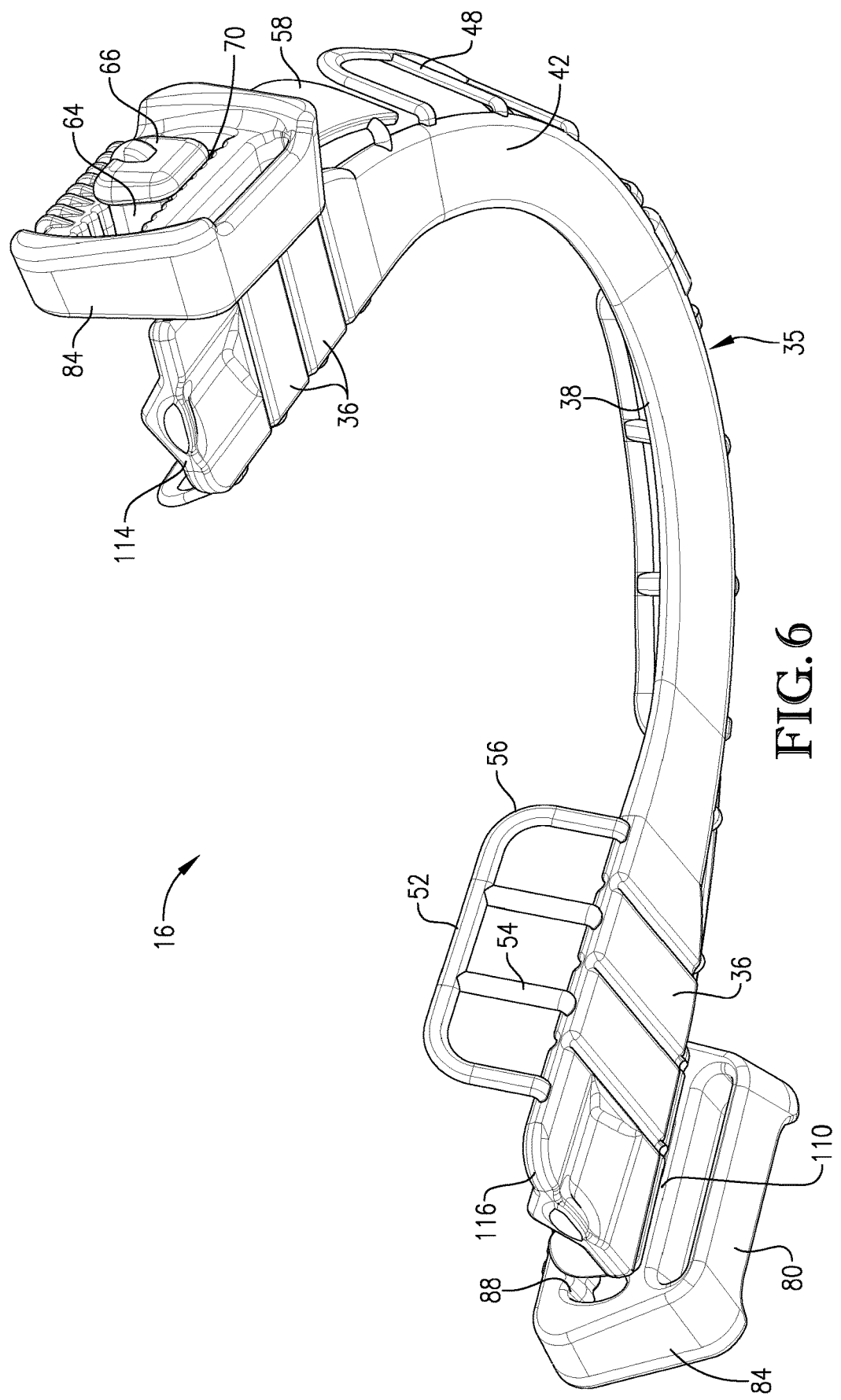
FIG. 6 is a bottom perspective view of the upper tray's inner core and adjustment members.

Turning to FIGS. 5-7, inner core 16 generally comprises an arch 35 that includes a pair of bite pad segments 36 that are interconnected by an anterior arch segment 38. It is noted that arch segment 38 and bite pad segments 36 need not necessarily be in the form of discrete components, but rather they can form unitary sections of a core structure that do not have well-defined transitional sections between said segments. Each bite pad segment 36 and the arch segment 38 comprise an occlusal surface 40 that is configured to face a wearer's maxillary teeth and an opposed inferior surface 42. In preferred embodiments, the bite pad occlusal surface slopes outwardly and downwardly at an angle of approximately 3° from horizontal. The arch segment 38 has an occlusal or bite surface that is sloped downwardly toward the anterior in order to compliment the natural shape of the wearer's anterior teeth. In preferred embodiments, the occlusal surface of arch segment 38 has a slope of approximately 33° from horizontal at its steepest point. These surfaces are configured to be overmolded by portions of outer layer 18 that are configured to contact the user's maxillary teeth. In order to assist with the overmolding process, a plurality of offsets 44 extend from the occlusal surface 40. These offsets 44 are configured to provide space within the mold of an injection molding machine for the thermoplastic material of the outer layer to flow around and substantially cover or envelop the occlusal surface 40. In addition, offsets 44 may serve as molar occlusal groove locators which further assist the user in proper fitting of device 10.

Positioning elements 46 extend upwardly from bite pad segments 36 and are adapted to be received in the occlusal groove between the buccal and lingual cusps of a maxillary molar, preferably the first molar. Positioning elements 46 assist with proper alignment of upper tray 12 within the user's mouth during the custom-forming process.

Inner core 16 comprises several lattice segments that extend in a superior direction from the arch and bite pad segments. These lattice segments provide support to the various outer layer sidewalls 24, 26, 28, especially during the fitting process in which the outer layer material is softened and then conformed to the wearer's maxillary teeth. These lattice segments provide structural integrity to the surrounding portions of outer layer 18 to avoid collapse of these sidewalls and assist the wearer in achieving a comfortable fit. In addition, these lattice structures create a constraint against shrinkage of the outer layer 18 post-fitting.

In the embodiment illustrated in FIGS. 5-7, core 16 comprises a pair of anterior, facial lattice segments 48 disposed on opposite sides of an anterior stop 50. It was discovered that by preferably making lattice segments 48 independent from each other (as opposed to a single continuous network) the flexibility of the tray 12 was improved and made for more secure fitment of the tray. Anterior stop 50 preferably extends from core 16 at an angle of approximately 90-100°, preferably 94°, relative to horizontal. Core 16 also comprises a pair of lingual lattice segments 52 extending upwardly from bite pad segments 36. The lattice segments 48, 52 are preferably formed from the same material as the other portions of core 16. However, the lattice segments generally are much thinner than the other portions of the core so as to present greater flexibility than the rest of the core. The lattice segments comprise a network of interconnected, generally wire-like rectilinear members 54 and/or curvilinear members 56 that are unitary and not independent from each other. In certain embodiments, the lattice segments are formed simultaneously with the other portions of core 16 during, for example, an injection molding process. In certain embodiments, the lingual and/or buccal surfaces of members 54, 56 are flat as opposed to being rounded. This configuration helps in making the lattice segments more flexible and easier to form around the maxillary teeth of the wearer. The lattice segments 48, 52 generally extend upwardly and outwardly from respective bite pad 36 and arch segments 38 at an angle of approximately 110° relative to horizontal (i.e., 20° relative to vertical) to be more open and accommodating during the fitting process. In preferred embodiments, the various lattice segments 48, 52 are independent from each other, thus permitting the greatest degree of freedom during fitting of upper tray 12 to the wearer's maxillary arch.

Core 16 further comprises a buccal wall 58 extending from each bite pad segment 36. Unlike the lattice segments, the buccal walls 58 are generally solid, continuous wall sections. Buccal walls 58 may extend completely along the sides of the bite pad segments 36 and along a portion of the side of the arch segment 38. As illustrated, it is preferred for the buccal walls to follow the contours of the bite pad segments 36 and arch segment 38. In certain embodiments, buccal walls 58 are configured to extend from the wearer's first molar forward, wrapping around the first molar and at least one of the wearer's premolars toward the midline of the maxillary arch. Buccal walls 58 extend upwardly from bite pad segments 36 at an angle of approximately 100° relative to the horizontal. This angular orientation approximates the natural taper of the posterior buccal proximal to the distal tooth face and provides optimal positioning for the post, stop, and fin, described below. In addition, the buccal sidewall distal end is oriented at an angle of approximately 15-20°, and preferably approximately 18°, relative to the centerline of the upper tray. Each buccal wall comprises a window section 60, which presents as a cut-out or recessed portion of the wall. The lower margin of window section 60 is defined by a sill 62. A post 64 extends laterally from each buccal wall 58, preferably below the sill 62, and includes a button 66 located at the outboard end thereof. In certain embodiments, the longitudinal axis of post 64 extends outwardly from buccal wall 58 at an angle of about 70-75°, and preferably about 72°, relative to the centerline of the upper tray. Each post comprises a superior surface 68 and an inferior surface 70. Preferably, surfaces 68 and 70 are contoured or scalloped along at least a portion of the length thereof. The purpose of these scallops is discussed below. Preferably, posts 64 and buttons 68 are not overmolded with outer layer 18, although this need not always be the case.

In preferred embodiments, each button 66 comprises a parting line 72 that is substantially even with the sill 62, and particularly the lowest edge of sill 62. The length of the button, L, is the greatest at the parting line 72 and decreases above and below the parting line 72. Preferably, each button 66 comprises a face 74 that slopes downward and inwardly toward the buccal sidewall 58. Thus, the length of the inferior surface 72 of post 64 may be less than the length of superior surface 68. The function of these various structures is described in greater detail below.

Upper tray 12 further comprises a pair of adjustable stop members 76 that are slidably attached to respective posts 64. As shown, for example, in FIGS. 12 and 13, stop members 76 have a generally trapezoidal shape and comprise a superior edge 78, an inferior edge 80, and opposed side edges 82, 84. In preferred embodiments, stop members 76 are symmetrical so that the stop member can be attached to either of posts 64. Stop members 76 also comprise an adjustment slot 86 that is adapted to engage the superior and inferior surfaces of post 64. Adjustment slot 86 includes opposed inner margins 88, 90 that are configured to mate with the superior surface 68 and inferior surface 70 of post 64. Particularly, the inner margins of slot 86 are scalloped in a similar manner as surfaces 68, 70. Thus, the crest 92 of surfaces 68, 70 are configured to mate with a trough 94 of margins 88, 90, and a trough 96 of surfaces 68, 70 are configured to mate with the crest 98 of margins 88, 90.

It is noted that adjustment slot 86 is slightly elastically deformable to allow for respective crests and troughs to slide over each other so that stop member 76 may be advanced in an anterior or posterior direction as desired. In particular embodiments, the period of scalloped surfaces 68, 70 and margins 88, 90 (i.e., the distance between crests or troughs) is approximately 1 mm. Thus, the stop member 76 be advanced relative to post 64 (and the upper tray in general) in increments of 1 mm. Button 66 comprises an arrow 100 that points toward a plurality of indexing marks 102 on the stop member 76 to assist the wearer with identifying the position of stop member 76 relative to post 64. Note, the ends 104 and 106 of slot 86 are rounded. It was discovered that in embodiments that did not possess this rounded geometry, the force required to advance stop member 76 varied considerably depending upon the position of the stop member relative to post 64. However, by providing the rounded geometry at ends 104, 106, stop member 76 was slightly weakened which provided a more consistent grip of post 64 across all indexing positions.

Stop member 76 also comprises a secondary slot 108 that is laterally spaced from and substantially parallel to the adjustment slot 86. Secondary slot 108 ensures that the stop member 76 uniformly compresses the superior and inferior surfaces of post 64. Thus, the bridge 110 formed between secondary slot 108 and adjustment slot 86 is substantially similar in width as the portion of stop member 76 that resides above adjustment slot 86. This feature ensures substantially similar resistance to deformation of both slot margins 88, 90. This feature also permits stop member side edges 82, 84 to be of a greater length, which, as explained below, contributes to the comfort and usefulness of the mandibular advancement device 10.

The stop members 76 are configured to be mounted on posts 64 following overmolding of upper tray 12 with outer layer 18. The presence of secondary slot 108 and the configuration of button 66 help facilitate this attachment. It is noted that buttons 66 comprises corners having certain radii of curvature rather than being truly square corners. It is important that stop member 76, post 64, and button 66 fit snugly together, because if they are too loose, device 10 will fail to retain lower tray 14 in the desired advanced position when worn. The corners of button 66 provide just enough clearance so that the button can be inserted into adjustment slot 86 and the stop member 76 slid over the button and onto post 64 without damaging or otherwise permanently deforming the top member, button, or post. In certain embodiments, the corners of buttons 66 have radii of curvature of approximately 0.03 inch. As shown in FIG. 7a, stop members 76 further comprise sloped inset regions 79, 81 disposed on the lingual side of the stop member and above and below adjustment slot 86. These sloped insets assist in assembling stop members 76 onto posts 64. In certain embodiments, the upper sloped inset region 79 has a slope that is less than the slope of the lower sloped inset region 81. In an exemplary embodiment, the upper sloped inset region 79 has a slope of approximately 115° from horizontal, and the lower sloped inset region 81 has a slope of approximately 130° from horizontal.

In certain embodiments, it is desirable for stop member 76 to remain in a substantially parallel relationship with buccal sidewall 58 throughout the stop member's path of travel. Button 66 can be configured to slope toward the buccal sidewall 58 in the downward direction so that the inboard surface of button lower lip 112 engages bridge 110 and holds it firmly up against the upper tray 12.

It is noted that core 16 has posterior end margins 114, 116 that are configured not to extend past (in a posterior direction) the wearer's first molars. By ending core 16, and consequently outer layer 18, at this location, room is left so that stop member 76 can be comfortably positioned in its setting of least mandibular advancement, which necessarily requires stop member 76 to extend past the first molar and proximate the wearer's second molar.

Core 16, and in particular bite pad segments 36, comprise a plurality of transverse hinges 118 that divide the bite pad segments into a plurality of hinged section 120. Hinges 118 permit pivoting of at least one hinged section 120 relative to another hinged section, which provides for enhanced customization of the upper tray 12 to the user's occlusal pattern, which leads to greater comfort of use.

Figure 8:
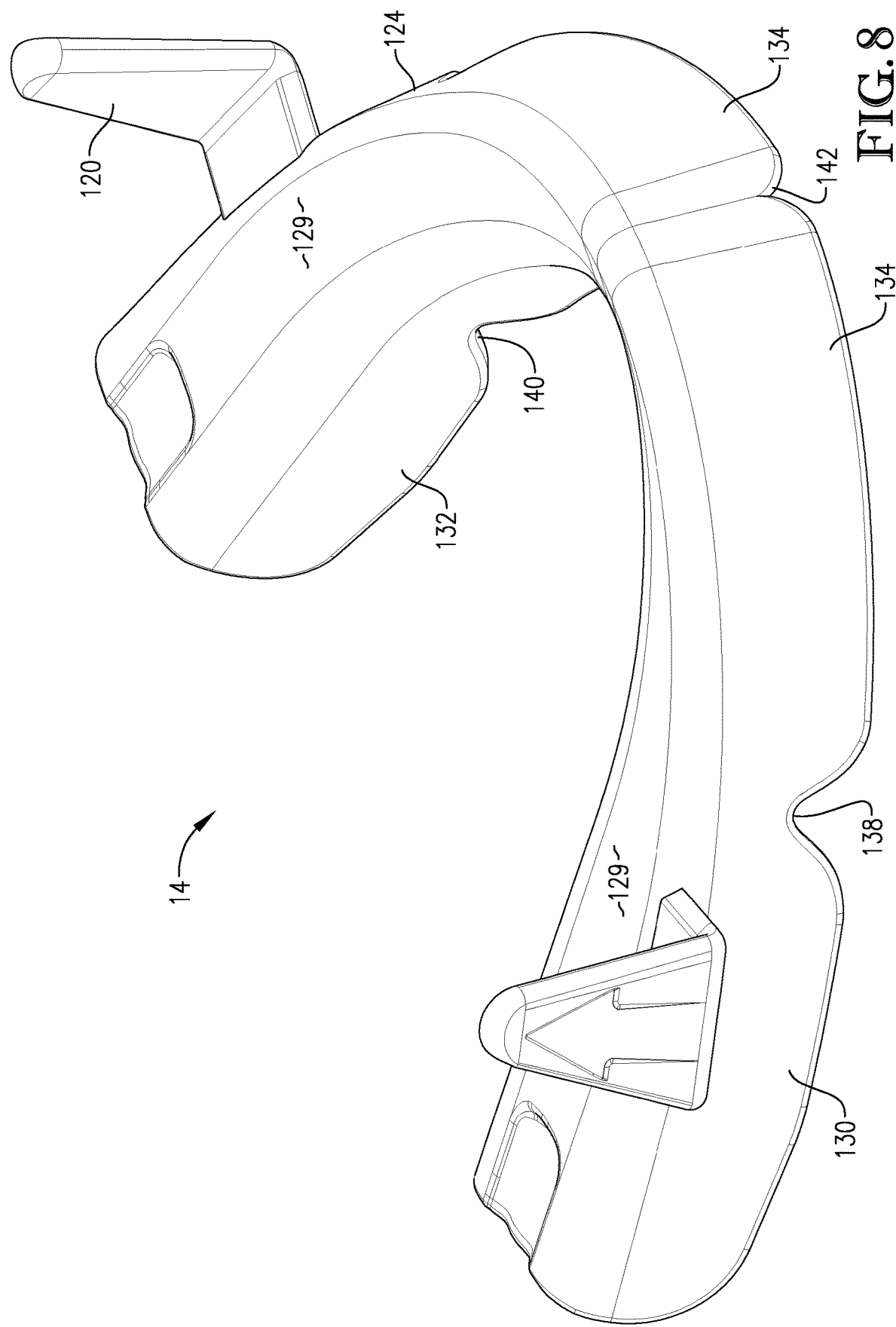
FIG. 8 is a top perspective view of the lower tray of the mandibular advancement device of FIG. 1.
Figure 9:
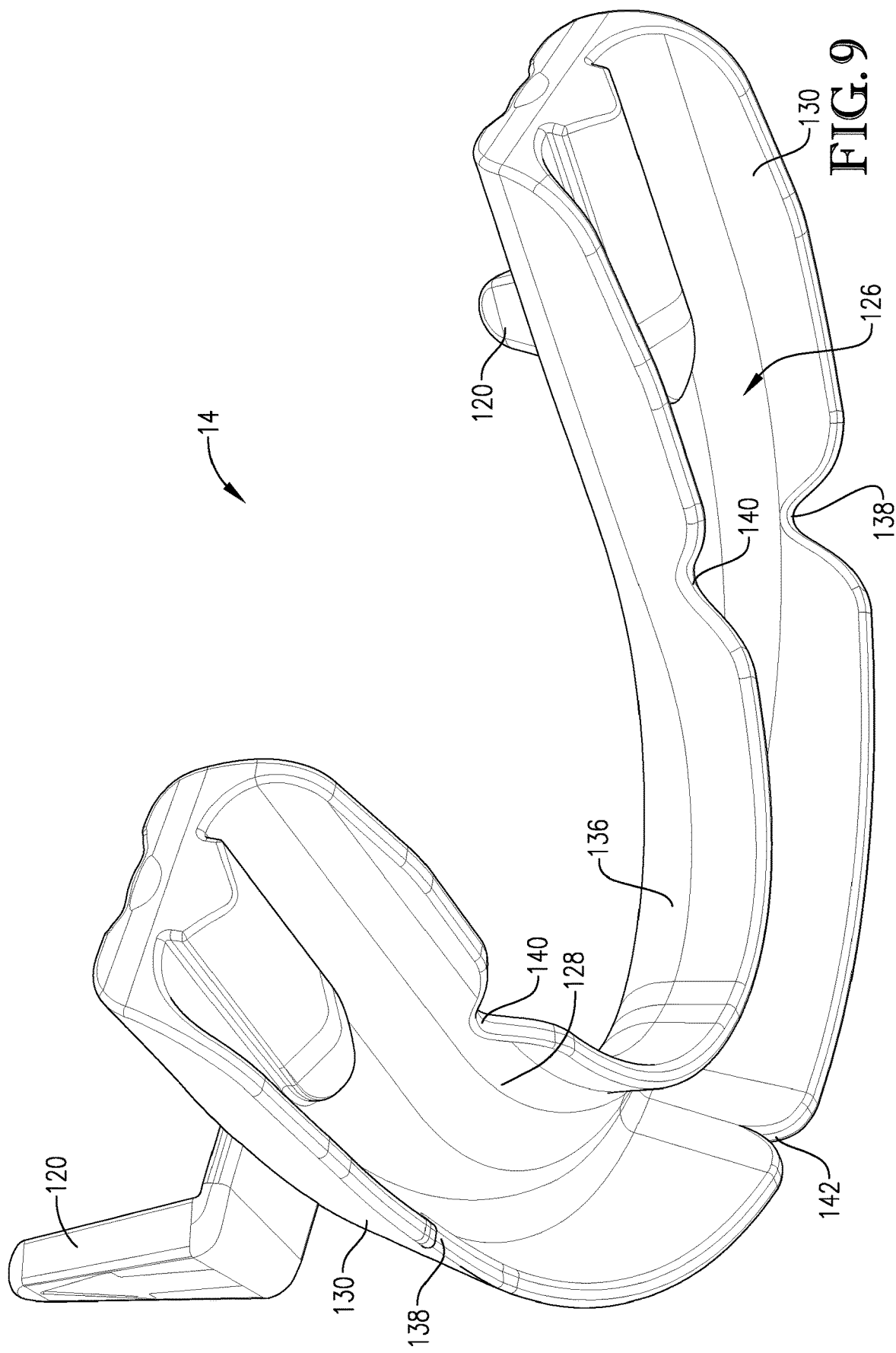
FIG. 9 is a bottom perspective view of the lower tray of the mandibular advancement device of FIG. 1.

Turning to FIGS. 8 and 9, lower tray 14 is adapted to be fitted over the user's mandibular arch and is constructed in a similarly to upper tray 12 in many respects. However, instead of having an adjustable stop member, and its associated structures, lower tray 14 comprises a pair of fins 120 that extend laterally from the lower tray.

Much like upper tray 12, lower tray 14 comprises an inner core 122 that is overmolded by an outer layer 124. The same materials used for inner core 16 and outer layer 18 may also be used to construct inner core 122 and outer layer 124, although this need not always be the case.

The outer layer 124 is configured to define, at least in part a channel 126 that is adapted to receive at least some of the mandibular teeth of a user. The channel 126 comprises a mandibular occlusal surface 128, and preferably buccal sidewalls 130 and lingual sidewalls 132. In certain embodiments, lower tray 14 further comprises a facial sidewall 134 and an anterior palatal sidewall 136. The various sidewalls that assist in defining channel 126 are formable to the contours of the user's mandibular teeth during customization of the lower tray. Thus, tray 14 may further comprise labial recesses 138 in between buccal sidewalls 130 and the facial sidewall 134, and lingual recesses 140 in between lingual sidewalls 132 and anterior palatal sidewall 136. In addition, an anterior recess 142 may be provided between adjacent facial sidewalls 134. Recesses 138, 140, 142 provide space into which the thermoplastic material comprising the various sidewalls may be displaced during custom fitting of tray 14. In addition, recesses 138, 140, 142 provide passageways for drainage of saliva from the channel 126, as necessary.

Figure 10:
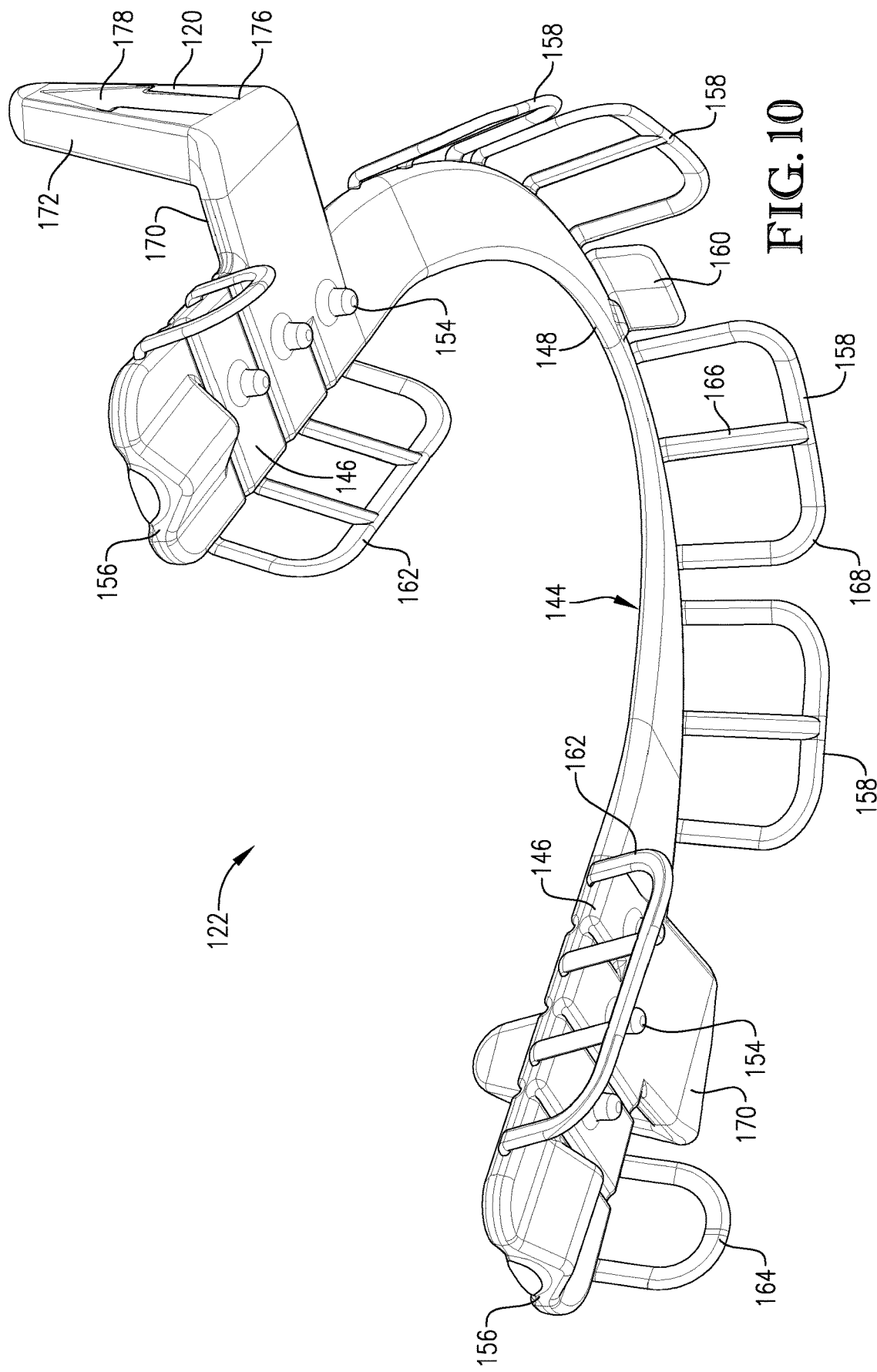
FIG. 10 is a bottom perspective view of the lower tray's inner core.
Figure 11:
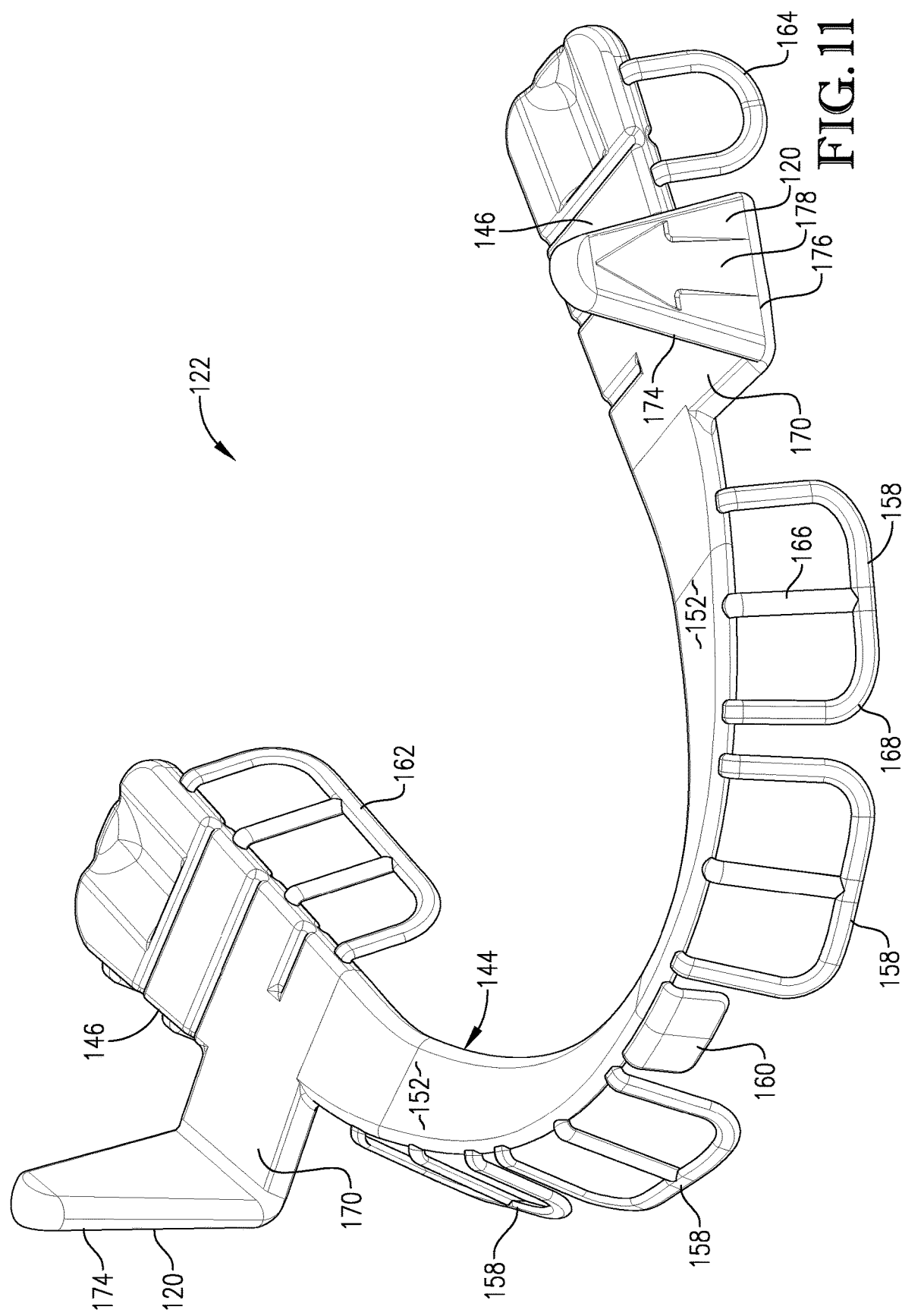
FIG. 11 is a top perspective view of the lower trays inner core.

As shown in FIGS. 10 and 11, inner core 122 generally comprises an arch 144 which includes a pair of bite pad segments 146 that are interconnected by an anterior arch segment 148. It is noted that arch segment 148 and bite pad segments 146 need not necessarily be in the form of discrete components, but rather they can form unitary sections of a core structure that do not have well-defined transitional sections between said segments. Each bite pad segment 146 and the arch segment 148 comprise an occlusal surface 150 that is configured to face a wearer's mandibular teeth and an opposed superior surface 152. The arch segment 148 has an occlusal surface that is sloped downwardly toward the anterior in order to provide a greater area of contact with the wearer's anterior teeth. These surfaces are configured to be overmolded by portions of outer layer 124 that are configured to contact the user's mandibular teeth. In order to assist with the overmolding process, a plurality of offsets 154 extend from the occlusal surface 150. These offsets 154 are configured to provide space within the mold of an injection molding machine for the thermoplastic material of the outer layer to flow around and substantially cover or envelop the occlusal surface 150. In addition, offsets 154 may serve as molar occlusal groove locators which further assist the user in proper fitting of device 10.

Positioning elements 156 extend downwardly from bite pad segments 36 and are adapted to be received in the occlusal groove between the buccal and lingual cusps of a mandibular molar, preferably the first molar. Positioning elements 156 assist with proper alignment of lower tray 14 within the user's mouth during the custom-forming process.

Inner core 122 comprises several lattice segments that extend in an inferior direction from the arch and bite pad segments. These lattice segments provide support to the various outer layer sidewalls 130, 132, 134 especially during the fitting process in which the outer layer material is softened and then conformed to the wearer's mandibular teeth. These lattice segments provide structural integrity to the surrounding portions of outer layer 124 to avoid collapse of these sidewalls and assist the wearer in achieving a comfortable fit. In addition, these lattice structures create a constraint against shrinkage of the outer layer 124 post-fitting.

In the embodiment illustrated in FIGS. 10 and 11, core 122 comprises a plurality of anterior, facial lattice segments 158 disposed on opposite sides of an anterior stop tab 160. Core 122 also comprises a pair of lingual lattice segments 162 extending downwardly from bite pad segments 146. Also extending downwardly from bite pad segments 146 are buccal lattice segments 164, which help support buccal wall 130. The lattice segments 158, 162, 164 are preferably formed from the same material as the other portions of core 122. However, the lattice segments generally are much thinner than the other portions of the core so as to present greater flexibility than the rest of the core. The lattice segments comprise a network of interconnected, generally wire-like rectilinear members 166 and/or curvilinear members 168 that are unitary and not independent from each other. In certain embodiments, the lattice segments are formed simultaneously with the other portions of core 122 during, for example, an injection molding process. In certain embodiments, the lingual and/or buccal surfaces of members 166, 168 are flat as opposed to being rounded. This configuration helps in making the lattice segments more flexible and easier to form around the mandibular teeth of the wearer. The lattice segments 158, 162, 164 generally extend downwardly and outwardly from respective bite pad 146 and arch segments 148 at an angle of approximately 110° relative to horizontal (i.e., 20° relative to vertical) to be more open an accommodating during the fitting process. In preferred embodiments, the various lattice segments 158, 162, 164 are independent from each other, thus permitting the greatest degree of freedom during fitting of lower tray 14 to the wearer's mandibular arch.

Fins 120 extend from respective bite pad segments 146 and are connected thereto by a lateral fin segment 170. In certain embodiments, the fins extend upwardly from bite pad segments 146 at an angle of approximately 90-100°, and preferably about 95°, from horizontal. Each of the fins 120 is configured to engage a respective stop member 76 to inhibit posterior movement of the lower tray 14 and, consequently, the wearer's mandible. In preferred embodiments, each of fins 120 is of generally triangular configuration and comprises a sloping posterior side margin 172 and a sloping anterior side margin 174. In certain embodiments, posterior side margin 172 slopes at an angle of approximately 100-105°, preferably approximately 103°, from horizontal. Side margins 172 are configured to engage the anterior side edges 82 of respective stop members 76. When the fins 120 and stop members 76 are engaged, it is preferable for the fin to extend in a superior direction past the superior edge 78 of stop member 76, and for the inferior edge 80 of stop member 76 to extend in an inferior direction past a fin lower margin 176. These dimensions of the fin 120 and stop member 76 permit the wearer to open his or her mouth to allow the wearer to better speak, breath, or drink fluids while wearing the device and still provide adequate overlap between side margin 172 and side edge 82 to maintain the wearer's mandible in an advanced position. As with posts 64 and stop members 76, it is preferable for fins 120 to not be overmolded with the outer layer 124, although this need not always be the case. In addition, fins 120 can bear a directional arrow 178 to assist the wearer in properly orienting lower tray 14 in his or her mouth.

As noted above, upper tray 12 and lower tray 14 comprise cores 16, 122 formed from a polymeric material that is different than the thermoplastic material comprising outer layers 18, 124. In particular embodiments, the core material has a softening point temperature that is higher than the softening point temperature of the thermoplastic material of the outer layer. As used herein, the term "softening point temperature" can refer to the melting point of the particular material, or the temperature at which the material otherwise loses its rigidity and becomes highly pliable and capable of being molded to the contours of a user's teeth. In certain embodiments, the thermoplastic material of the outer layer has a softening point temperature of less than 90° C., less than 80° C., or less than 70° C. In alternate embodiments, the thermoplastic material of the outer layer has a softening point temperature of from about 40° C. to about 80° C., about 45° C. to about 75° C., or from about 50° C. to about 70° C. In preferred embodiments, the thermoplastic material of the outer layer has a softening point temperature of about 60° C. In certain embodiments, the polymeric material of the core has a softening point temperature of at least 80° C., at least 85° C., or at least 100° C.

In certain embodiments, the outer layer comprises a thermoplastic elastomer, such as polycaprolactone, ethylene vinyl acetate, and various thermoplastic polyurethanes. In preferred embodiments, the outer layer comprises a resin blend, such as a homogeneous blend of polycaprolactone and EVA, polypropylene, or polyethylene. The polymer resin added to the polycaprolactone, for example, reduces the crystallinity of the material following the injection molding process and/or other thermal processing of the appliance that results in softening or melting of the polycaprolactone material, such as during custom fitting of the device by the end user. Reducing the crystallinity avoids or lessens the shrinkage of the material following any thermal processing of the device. In one particular embodiment, the outer layer comprises a substantially homogeneous 70/30 blend of polycaprolactone/ethylene vinyl acetate. It is noted that the lattice segments described above further help in reducing shrinkage of the trays around the teeth.

The core may also comprise a nylon, polyurethane, polypropylene, polyethylene, polyester, or methacrylate resin material. Nylon is a particularly preferred material for the core as it has a lower durometer value and higher flexural modulus which makes for better fitting comfort, lattice flex, and bite accommodation. Additionally, nylon has higher lubricity and, therefore, more abrasion resistance. As an added benefit, nylon raw materials can be less expensive than some of the alternative materials. In addition, the core may be formed from a polycaprolactone material or resin blend similar to that used in the outer layer; however, in such embodiments, the core polycaprolactone material would have a different melt profile temperature than that used for the outer layer. In certain embodiments, the outer layer and/or core may comprise additives or reinforcing materials embedded within the plastic and/or resin materials making up the respective structure thereby improving one or more physical properties of the materials, such as increasing the tensile strength, lowering the material melting point, lowering the coefficient of friction for the material, or interfering with the crystallization of the materials. For example, the materials may include glass or polytetrafluoroethylene additives that can improve the abrasion resistance of the material. Exemplary additives in this regard include glass fibers or particles, polytetrafluoroethylene, fluorinated ethylene propylene, starches, talc, calcium silicates, calcium carbonate and foaming additives, such as FOAMAZOL 90 (a blend of citric and carbonic salts). Of course, other additives may be added to the plastic or resin materials in order to impart desired characteristics as known and expected by one skilled in the art. For example, water could be added to the polycaprolactone material in order to inhibit crystallization of the polycaprolactone during manufacture. The polymeric core material is highly durable and resistant to wear caused by contact with the user's teeth during use of device 10. It is noted that the stop members 76 may be formed of the same material as the core or from a more rigid material if desired (e.g., taken from the list of core resins recited above).

Mandibular advancement devices 10 made in accordance with the present invention are useful in the treatment of obstructive sleep apnea and snoring that is often symptomatic of this condition. Prior to use, the device 10 can be custom fitted to the maxillary and mandibular arches of the user to provide a custom-formed device that approximates the fit of a clinical device. Custom fitting begins by heating both the upper and lower trays 12, 14 to a temperature less than the boiling point of water, preferably no greater than 85° C., and more preferably between about 40° C. to about 80° C., in order to soften at least a portion of the trays, particularly the outer layers 18, 124. Heating of the trays 12, 14 may be accomplished by immersing the trays in hot, but not boiling, water. The hot water may be obtained from the hot water tap connected to a typical residential water heater. Alternatively, tepid water can be heated, for example, in a microwave oven until it reaches the desired temperature, which should be very close to the softening point temperature of the thermoplastic material forming the outer layer 18, 124. In certain embodiments, upon reaching the softening point temperature, the outer layer turns translucent (whereas below the softening point temperature the outer layer is opaque). At this point, the user can be assured that the trays have been heated sufficiently.

The user then places the softened trays 12, 14, preferably one at a time, within his or her mouth as follows. The upper tray 12 is positioned so that at least some of the user's maxillary teeth reside within and contact at least one surface the channel 20. In addition, positioning element 46, if present, may be placed within the occlusal groove between the buccal and lingual cusps of a maxillary molar. Also, anterior stop tab 50 may become engaged with the user's anterior maxillary teeth to prevent tray 12 from being inserted too deeply into the user's mouth. The lower tray 14 is positioned so that at least some of the user's mandibular teeth reside within and contact at least one surface of the channel 126. In addition, positioning element 156 may be placed within the occlusal groove between the buccal and lingual cusps of a mandibular molar. Anterior stop tab 160 may also become engaged with the user's anterior mandibular teeth to prevent tray 14 from being too deeply inserted into the user's mouth. During the fitting process, it is preferred that the user's mandibular teeth do not engage with upper tray 12, or the user's maxillary teeth with lower tray 14. Thus, it is preferably for the inferior surface 23 of upper tray 12 and the superior surface 129 of lower tray 14 to be devoid of occlusal marks so that these surfaces may lie flush with each other when being worn by the user. However, in certain embodiments, it may be desirable for the user's teeth to lightly engage these surfaces during the fitting process to ensure a good fit is achieved. Also, it is within the scope of the present invention for special fitting trays to be used to aid in correct positioning of trays 12 and 14 within the user's mouth. Trays 12 and 14 would be placed in, or be carried by, these fitting trays, and the nested trays placed within the user's mouth around the appropriate arch. The fitting trays would then be discarded after fitting was completed.

During the fitting process, the user may also apply pressure to the various sidewalls of the upper and lower trays so that the sidewalls conform to the vestibular and palatal portions of the user's maxillary and mandibular teeth, again, giving the device 10 a clinical fit. Before removing the trays from his or her mouth, the user permits the softened outer layer to cool below its softening point temperature and harden.

Figure 12:
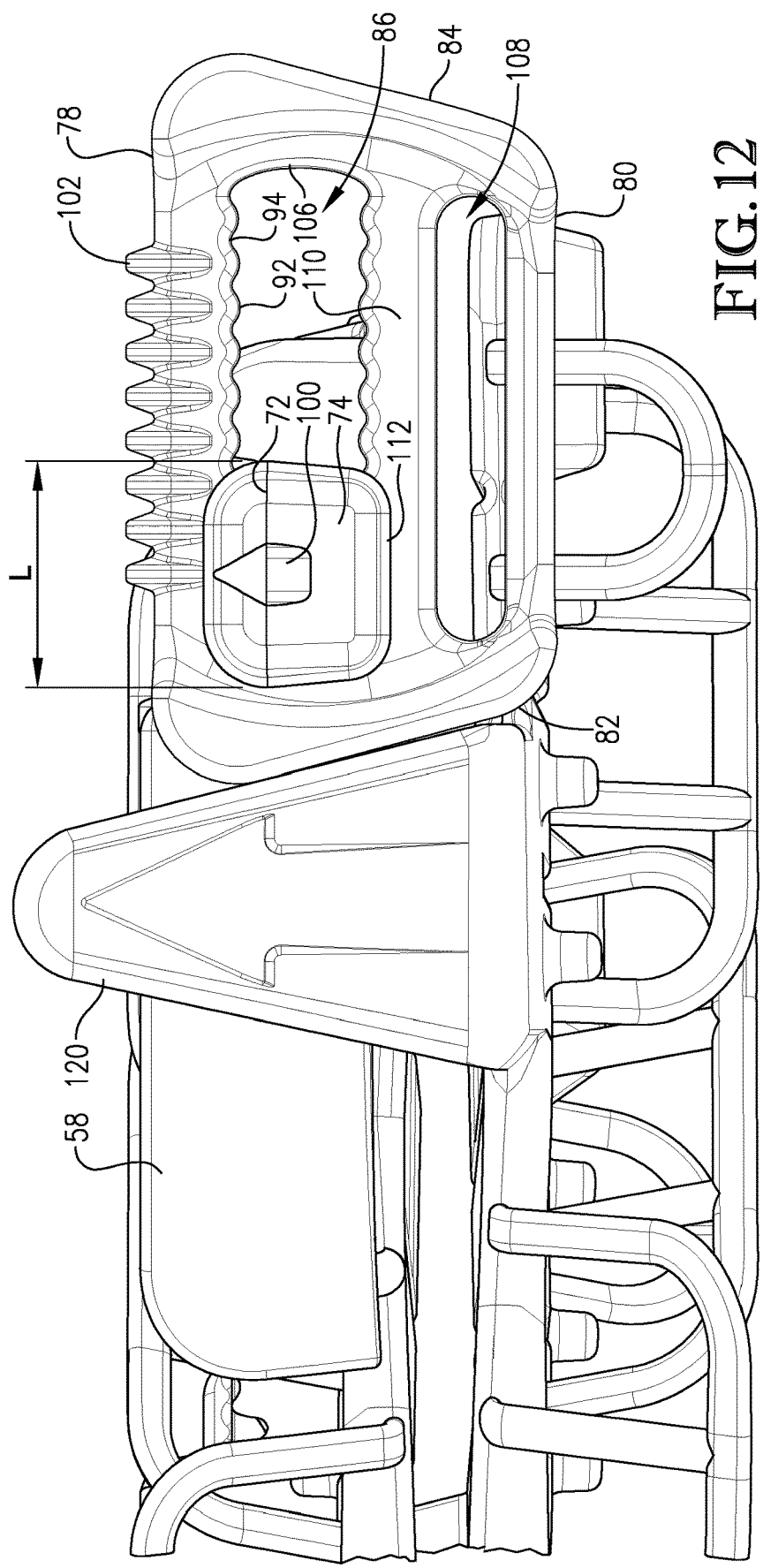
FIG. 12 is a side elevational view of the mandibular advancement device, with the outer layers removed, and the stop member in position of minimal mandibular advancement.
Figure 13:
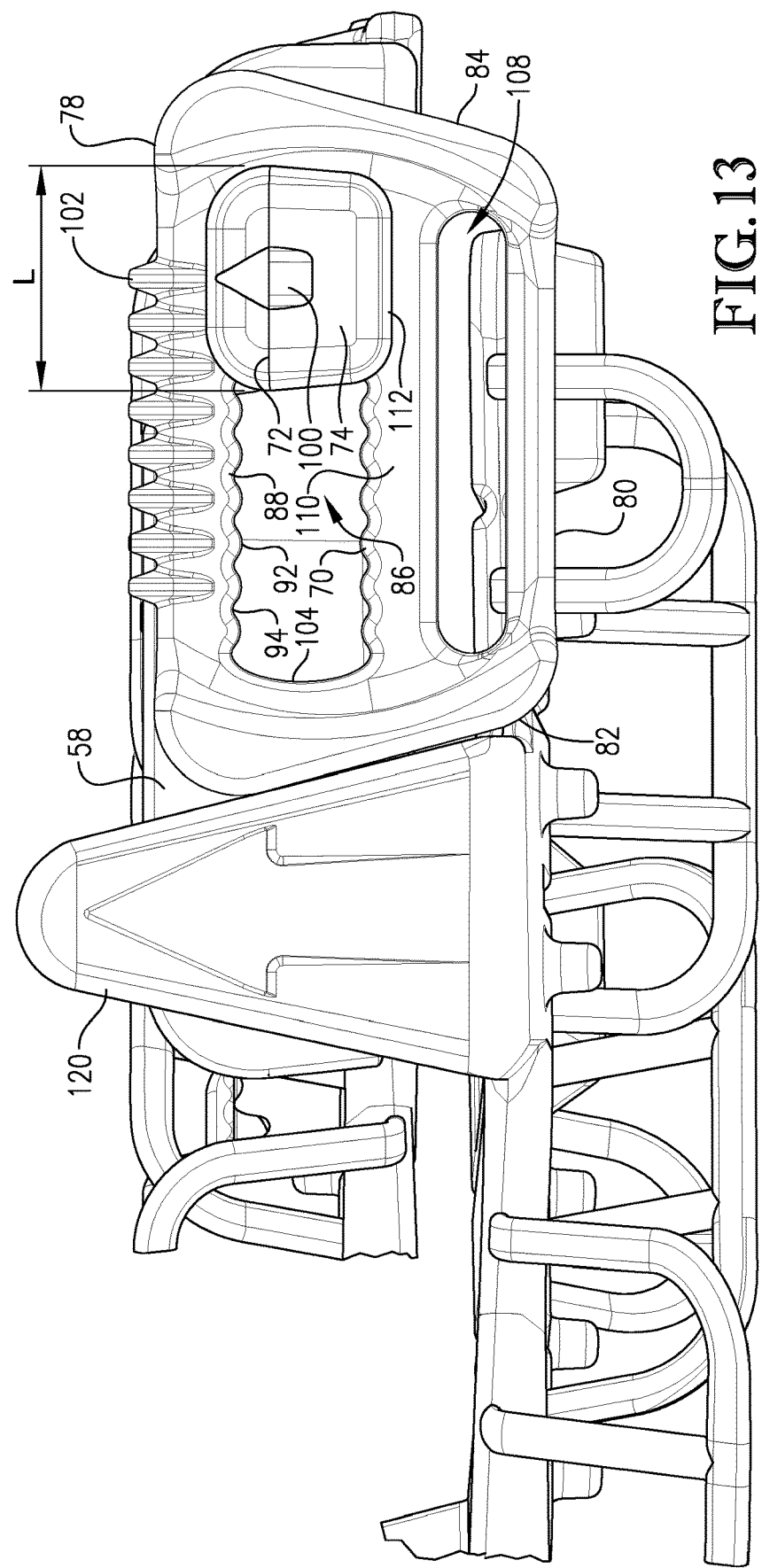
FIG. 13 is a side elevational view of the mandibular advancement device, with the outer layers removed, and the stop member in position of maximum mandibular advancement While the drawings do not necessarily provide exact dimensions or tolerances for the illustrated components or structures, the drawings are to scale with respect to the relationships between the components of the structures illustrated in the drawings.

Once the upper tray has hardened, the adjustable stop members 76 can be appropriately indexed so as to set the desired degree of mandibular advancement. As can be seen in FIG. 12, stop member 76 is shifted to its most posterior position. This position represents a "neutral" position in which there is substantially no mandibular advancement. In mild cases of snoring or obstructive sleep apnea, the user may find it sufficient to simply retain the mandible in a neutral position. Device 10 then primarily serves the function of maintaining the mandible in this normal or natural position during sleep and avoiding posterior shifting of the mandible which risks constricting the user's airway. In more severe cases of obstructive sleep apnea, the user will likely require that the mandible be advanced forward of its regular or neutral position in order to more fully open the user's airway. The stop members 76 can be indexed in an anterior direction in preferred increments of 1 mm. As illustrated, stop member 76 can achieve a maximum of 7 mm of mandibular advancement; however, other lengths are within the scope of the present invention. FIG. 13 depicts the shifting of stop member 76 into this maximum advancement position. As previously described, the adjustment slot 86 and post superior and inferior surfaces 68, 70 comprise interlocking surfaces that are configured to maintain the position of the stop member 76 relative to the post 64 despite the force applied to it by fin 120 when the device is in use.

I claim:

1. A mandibular advancement device comprising:
   an upper tray adapted to be fitted over a user's maxillary arch and comprising a pair of adjustable stop members; and
   a lower tray adapted to be fitted over the user's mandibular arch and comprising a pair of fins extending from the lower tray, each of the fins being configured to engage a respective stop member to inhibit posterior movement of the lower tray when worn by the user,
   each of the upper and lower trays comprising a core formed from a first material having a first softening point temperature and an outer layer overmolded onto the core, the outer layer being formed from a second material having a second softening point temperature that is less than the first softening point temperature;
   wherein the upper tray comprises a pair of posts extending late rally from respective buccal side walls of the upper tray core, each post including a button disposed at an outboard end thereof;
   wherein each post comprises superior and inferior surfaces adapted to engage an adjustment slot formed in the stop members, the adjustment slot comprising opposed scalloped inner margins configured to mate with the superior and inferior surfaces of each post;
   wherein each stop member comprises a secondary slot that is laterally disposed from and substantially parallel to the adjustment slot.

2. The mandibular advancement device of claim 1, wherein the scalloped margins have a period of approximately 1 mm.

3. The mandibular advancement device of claim 1, wherein the posts and buttons are not overmolded with the outer layer.

4. The mandibular advancement device of claim 1, wherein each of the buccal sidewalls comprise a window section formed therein, wherein the window section comprises a sill that is disposed below an upper margin of the buccal sidewall, the posts extending from the buccal sidewalls below the sill.

5. The mandibular advancement device of claim 4, wherein each button comprises a parting line that is substantially even with the sill, wherein a length of the button is the greatest at the parting line and decreases above and below the parting line.

6. The mandibular advancement device of claim 1, wherein each button slopes inwardly toward the buccal side wall.

7. The mandibular advancement device of claim 1, wherein the upper tray core comprises an arch and buccal and lingual lattice segments extending from the arch, wherein the buccal lattice segments are positioned to an anterior of the buccal sidewalls, and the lingual lattice segments are positioned opposite the buccal sidewalls.

8. The mandibular advancement device of claim 7, wherein the arch comprises a pair of posterior bite pad segments interconnected by an anterior arch segment.

9. The mandibular advancement device of claim 8, wherein the lingual lattice segments extend from the bite pad segment, and the buccal lattice segments extend from the anterior arch segment.

10. The mandibular advancement device of claim 9, wherein the anterior arch segment comprises a sloped bite surface.

11. The mandibular advancement device of claim 8, wherein the anterior arch segment comprises an anterior stop tab located in between adjacent buccal lattice segments.

12. The mandibular advancement device of claim 1, wherein each fin comprises a posterior margin that is configured to engage an anterior side edge of the stop member.

13. The mandibular advancement device of claim 1, wherein the fins are not overmolded with the outer layer.

14. The mandibular advancement device of claim 1, wherein the lower tray core comprises an arch segment and buccal and lingual lattice segments extending therefrom.

15. The mandibular advancement device of claim 14, wherein the lower tray core comprises an anterior stop tab extending from the arch segment, the lower tray core comprising at least one buccal lattice segment positioned to each side of the anterior stop tab along the arch segment.

16. A method of treating obstructive sleep apnea comprising:

fitting the mandibular advancement device of claim 1 to the maxillary and mandibular arches of a user, the fitting step comprising heating the upper and lower trays to a temperature of about 40° C. to about 80° C. thereby causing the overmolded outer layer of each tray to soften, molding the softened outer layer of the upper tray to at least some of the user's maxillary teeth, and molding the softened outer layer of the lower tray to at least some of the user's mandibular teeth;

permitting the softened outer layer of the upper and lower trays to harden within the user's mouth; and adjusting the pair of adjustable stop members to maintain the mandible in an advanced position when the device is being worn by the user.

* * * * *